US011035481B2

United States Patent
Schaeffer et al.

(10) Patent No.: US 11,035,481 B2
(45) Date of Patent: *Jun. 15, 2021

(54) BI-DIRECTIONAL VALVE DEVICE FOR SELECTIVE CONTROL OF FLUID FLOW THROUGH MULTIPLE CONVERGING PATHS

(71) Applicant: Cook Medical Technologies LLC, Bloomington, IN (US)

(72) Inventors: Darin Schaeffer, Bloomington, IN (US); Jeffry Melsheimer, Springville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 319 days.

This patent is subject to a terminal disclaimer.

(21) Appl. No.: 15/990,683

(22) Filed: May 27, 2018

(65) Prior Publication Data

US 2018/0274688 A1 Sep. 27, 2018

Related U.S. Application Data

(63) Continuation of application No. 15/174,220, filed on Jun. 6, 2016, now Pat. No. 9,982,791, which is a
(Continued)

(51) Int. Cl.
*A61M 39/28* (2006.01)
*A61M 1/00* (2006.01)
(Continued)

(52) U.S. Cl.
CPC .......... *F16K 11/14* (2013.01); *A61M 1/0064* (2013.01); *A61M 39/287* (2013.01);
(Continued)

(58) Field of Classification Search
CPC ..... F16K 7/02; F16K 7/04; F16K 7/06; F16K 7/063; F16K 7/065; F16K 7/066;
(Continued)

(56) References Cited

U.S. PATENT DOCUMENTS

| 486,698 A | 11/1892 | Ketchum |
| 1,686,003 A | 10/1928 | Hottinger |

(Continued)

FOREIGN PATENT DOCUMENTS

| GB | 2100842 | 1/1983 |
| WO | WO2004096061 | 11/2004 |
| WO | WO2013036732 | 3/2013 |

OTHER PUBLICATIONS

Cook Medical Incorporated, Accessories for Endovascular Graft Procedures, 2007, p. 1-28.
(Continued)

*Primary Examiner* — David Colon-Morales
(74) *Attorney, Agent, or Firm* — MacMillan, Sobanski & Todd, LLC

(57) ABSTRACT

Hand-operated suction and irrigation medical devices are provided. An example medical device comprises a housing having a proximal end and a distal end. The housing defines first and second inlet paths and an outlet path. A first tubular member is partially disposed within the first inlet path and a second tubular member is partially disposed within the second inlet path. Each of the first and second tubular members extends from the proximal end of the housing. A third tubular member is partially disposed within the outlet path and extends from the distal end of the housing. A control member is slidably disposed on the housing and is movable between a first, proximal position and a second, distal position. A passageway provides fluid communication between the first inlet path and an opening to an environment external to the housing such that covering the opening
(Continued)

provides control over the flow of fluid through the first inlet path and the first tubular member.

20 Claims, 5 Drawing Sheets

Related U.S. Application Data continuation of application No. 14/210,821, filed on Mar. 14, 2014, now Pat. No. 9,360,124.

(60) Provisional application No. 61/786,760, filed on Mar. 15, 2013.

(51) Int. Cl.
*A61M 39/22* (2006.01)
*F16K 11/14* (2006.01)
*F16K 7/06* (2006.01)

(52) U.S. Cl.
CPC .......... *A61M 2039/224* (2013.01); *F16K 7/06* (2013.01); *Y10T 137/87692* (2015.04); *Y10T 137/87708* (2015.04)

(58) Field of Classification Search
CPC ........ F16K 11/14; F16K 11/16; F16K 11/161; F16K 11/027; Y10T 137/87153; Y10T 137/87161; Y10T 137/87692; Y10T 137/87716; Y10T 137/87708; Y10T 137/87571; Y10T 137/87668; Y10T 137/87981; Y10T 137/87997; A61M 39/287; A61M 2039/224; A61M 1/0064; A61M 1/0062; A61M 1/0058
USPC ...................................................... 251/4–10
See application file for complete search history.

(56) References Cited

U.S. PATENT DOCUMENTS

| | | | |
|---|---|---|---|
| 2,812,765 A * | 11/1957 | Tofflemire | A61M 1/0064 604/32 |
| 2,985,192 A | 5/1961 | Taylor et al. | |
| 3,018,793 A | 1/1962 | Aagaard | |
| 3,411,534 A | 11/1968 | Rose | |
| 3,515,170 A | 6/1970 | Mullaly | |
| 3,533,439 A | 10/1970 | Hall | |
| 3,635,251 A | 1/1972 | Gaines | |
| 3,759,483 A | 9/1973 | Baxter | |
| 3,828,822 A | 8/1974 | Witte | |
| 3,900,184 A | 8/1975 | Burke et al. | |
| 3,918,490 A | 11/1975 | Goda | |
| 4,121,622 A | 10/1978 | Forberg | |
| 4,230,151 A | 10/1980 | Jonsson | |
| 4,262,876 A | 4/1981 | Willatt | |
| 4,484,599 A | 11/1984 | Hanover et al. | |
| 4,491,156 A | 1/1985 | Lee, II | |
| 4,502,508 A * | 3/1985 | Lester | A61M 1/0023 137/625.48 |
| 4,544,127 A | 10/1985 | Szabo | |
| 4,655,198 A | 4/1987 | Hommann | |
| 4,697,785 A | 10/1987 | Tuseth | |
| 4,852,551 A | 8/1989 | Opie et al. | |
| 4,875,897 A | 10/1989 | Lee | |
| 4,960,108 A | 10/1990 | Reichel et al. | |
| 4,971,039 A | 11/1990 | Noske et al. | |
| 4,972,826 A | 11/1990 | Koehler et al. | |
| 4,976,255 A | 12/1990 | Reichenberger et al. | |
| 4,979,500 A | 12/1990 | Hassler et al. | |
| 4,993,594 A | 2/1991 | Becker et al. | |
| 5,009,232 A | 4/1991 | Hassler et al. | |
| 5,031,626 A | 7/1991 | Hassler et al. | |
| 5,055,051 A | 10/1991 | Duncan | |
| 5,059,200 A | 10/1991 | Tulip | |
| 5,065,761 A | 11/1991 | Pell | |
| 5,065,762 A | 11/1991 | Ifflaender et al. | |
| 5,067,493 A | 11/1991 | Inbar et al. | |
| 5,081,984 A | 1/1992 | Wess et al. | |
| 5,082,025 A | 1/1992 | DeVries et al. | |
| 5,095,889 A | 3/1992 | Weissmuller et al. | |
| 5,113,906 A | 5/1992 | Hogner | |
| 5,129,910 A | 7/1992 | Phan et al. | |
| 5,133,338 A | 7/1992 | Wess et al. | |
| 5,135,534 A | 8/1992 | Tulip | |
| 5,152,768 A | 10/1992 | Bhatta | |
| 5,158,085 A | 10/1992 | Belikan et al. | |
| 5,167,637 A | 12/1992 | Okada et al. | |
| 5,195,508 A | 3/1993 | Muller et al. | |
| 5,195,509 A | 3/1993 | Rentschler et al. | |
| 5,199,950 A | 4/1993 | Schmitt et al. | |
| 5,211,625 A | 5/1993 | Sakurai et al. | |
| 5,219,401 A | 6/1993 | Cathignol et al. | |
| 5,224,929 A * | 7/1993 | Remiszewski | A61M 1/0064 137/596.2 |
| 5,233,980 A | 8/1993 | Mestas et al. | |
| 5,242,454 A | 9/1993 | Gundlach et al. | |
| 5,246,447 A | 9/1993 | Rosen et al. | |
| 5,256,160 A * | 10/1993 | Clement | A61B 18/1482 220/502 |
| 5,257,973 A | 11/1993 | Villasuso | |
| 5,263,076 A | 11/1993 | Elff et al. | |
| 5,269,772 A | 12/1993 | Wilk | |
| 5,290,294 A | 3/1994 | Cox et al. | |
| 5,309,904 A | 5/1994 | Beck | |
| 5,312,418 A | 5/1994 | Bonnet | |
| 5,347,997 A | 9/1994 | Weiler et al. | |
| 5,354,271 A | 10/1994 | Voda | |
| 5,383,896 A | 1/1995 | Gershony et al. | |
| 5,402,823 A | 4/1995 | Cole | |
| 5,425,735 A | 6/1995 | Rosen et al. | |
| 5,449,363 A | 9/1995 | Brust et al. | |
| 5,658,239 A | 8/1997 | Delmenico | |
| 5,746,736 A | 5/1998 | Tankovich | |
| 5,814,026 A | 9/1998 | Yoon | |
| 5,820,627 A | 10/1998 | Rosen et al. | |
| 5,830,195 A | 11/1998 | Peters et al. | |
| 5,836,898 A | 11/1998 | Schwieker | |
| 5,868,756 A | 2/1999 | Henry et al. | |
| 5,891,113 A | 4/1999 | Quinn | |
| 5,901,745 A | 5/1999 | Buchtel | |
| 5,906,623 A | 5/1999 | Peterson | |
| 5,919,183 A | 7/1999 | Field | |
| 5,944,687 A | 8/1999 | Benett et al. | |
| 5,963,575 A | 10/1999 | Muller et al. | |
| 5,997,497 A | 12/1999 | Nita et al. | |
| 6,066,150 A * | 5/2000 | Gonon | A61B 17/3203 604/22 |
| 6,099,506 A | 8/2000 | Macoviak et al. | |
| 6,113,560 A | 9/2000 | Simnacher | |
| 6,123,679 A | 9/2000 | Lafaut et al. | |
| RE37,024 E | 1/2001 | Brust et al. | |
| 6,217,588 B1 | 4/2001 | Jerger et al. | |
| 6,217,555 B1 | 5/2001 | Hart et al. | |
| 6,228,046 B1 | 5/2001 | Brisken | |
| 6,319,261 B1 | 11/2001 | Bowers | |
| 6,352,520 B1 | 3/2002 | Miyazaki | |
| 6,352,521 B1 | 3/2002 | Prosl | |
| 6,375,651 B2 | 4/2002 | Grasso, III et al. | |
| 6,440,123 B1 | 8/2002 | Engel | |
| 6,491,685 B2 | 12/2002 | Visuri et al. | |
| 6,536,739 B1 | 3/2003 | Jensen | |
| 6,589,197 B1 | 7/2003 | Doi et al. | |
| 6,620,172 B1 | 9/2003 | Dretler et al. | |
| 6,623,426 B2 | 9/2003 | Bonadio et al. | |
| 6,648,017 B2 | 11/2003 | Lamas et al. | |
| 6,652,547 B2 | 11/2003 | Rabiner et al. | |
| 6,726,681 B2 | 4/2004 | Grasso, III et al. | |
| 6,770,039 B2 | 8/2004 | Zhong et al. | |
| 6,932,788 B2 * | 8/2005 | Kamiyama | A61M 1/0062 604/43 |
| 6,936,025 B1 | 8/2005 | Evans et al. | |
| 7,025,741 B2 | 4/2006 | Cull | |

(56) References Cited

U.S. PATENT DOCUMENTS

| | | |
|---|---|---|
| 7,087,061 B2 | 8/2006 | Chernenko et al. |
| 7,104,983 B2 | 9/2006 | Grasso, III et al. |
| 7,527,058 B2 | 5/2009 | Wright et al. |
| 7,571,889 B2 | 8/2009 | Miyahara |
| 7,597,686 B2 | 10/2009 | MacMillan et al. |
| 7,637,877 B2 | 12/2009 | Hofmann et al. |
| 7,645,245 B2 | 1/2010 | Sekino et al. |
| 7,690,382 B2 | 4/2010 | Raif et al. |
| 7,736,328 B2 | 6/2010 | Childers et al. |
| 7,762,999 B2 | 7/2010 | Byrum |
| 7,775,206 B2 | 8/2010 | Anderson et al. |
| 7,878,202 B2 | 2/2011 | Anderson et al. |
| 8,152,780 B2 | 4/2012 | Evans et al. |
| 8,206,294 B2 | 6/2012 | Widenhouse et al. |
| 8,241,271 B2 * | 8/2012 | Millman ............ A61M 1/0058 606/1 |
| 8,419,783 B2 | 4/2013 | Frye et al. |
| 8,690,834 B2 | 5/2014 | Koehler |
| 9,192,514 B2 * | 11/2015 | Mita ................... A61M 5/178 |
| 9,360,124 B2 * | 6/2016 | Schaeffer ............... F16K 11/14 |
| 9,982,791 B2 * | 5/2018 | Schaeffer ............... F16K 11/14 |
| 2001/0031971 A1 | 10/2001 | Dretler et al. |
| 2002/0002366 A1 | 1/2002 | Grasso, III et al. |
| 2002/0058890 A1 | 5/2002 | Visuri et al. |
| 2002/0103477 A1 | 8/2002 | Grasso, III et al. |
| 2003/0093013 A1 | 5/2003 | Zhong et al. |
| 2003/0176873 A1 | 9/2003 | Chernenko et al. |
| 2004/0138594 A1 | 7/2004 | Sekino et al. |
| 2004/0167445 A1 | 8/2004 | Simnacher |
| 2004/0167559 A1 | 8/2004 | Taylor et al. |
| 2004/0186397 A1 | 9/2004 | Haumann |
| 2004/0225283 A1 | 11/2004 | Nahleili |
| 2004/0243123 A1 | 12/2004 | Grasso, III et al. |
| 2005/0004455 A1 | 1/2005 | Kaltschmidt |
| 2005/0038361 A1 | 2/2005 | Zhong et al. |
| 2005/0143678 A1 | 6/2005 | Schwarz et al. |
| 2005/0192593 A1 | 9/2005 | Dretler et al. |
| 2005/0232398 A1 | 10/2005 | Kopping et al. |
| 2006/0020269 A1 | 1/2006 | Cheng |
| 2006/0069349 A1 | 3/2006 | Ganz et al. |
| 2006/0084958 A1 | 4/2006 | Raif et al. |
| 2006/0142754 A1 | 6/2006 | Irion et al. |
| 2006/0189870 A1 | 8/2006 | Hofmann et al. |
| 2007/0016114 A1 | 1/2007 | Buchholtz et al. |
| 2007/0021754 A1 | 1/2007 | Chernenko et al. |
| 2007/0078395 A1 | 4/2007 | Valaie |
| 2007/0213765 A1 | 9/2007 | Adams et al. |
| 2007/0260266 A1 | 11/2007 | Karpiel |
| 2008/0009884 A1 | 1/2008 | Kennedy, II |
| 2008/0103481 A1 | 5/2008 | Vogel et al. |
| 2008/0188864 A1 | 8/2008 | Ducharme |
| 2008/0281199 A1 | 11/2008 | DeBrock et al. |
| 2009/0030378 A1 | 1/2009 | Garcia, Jr. |
| 2009/0163808 A1 | 6/2009 | Peyrard et al. |
| 2009/0204032 A1 | 8/2009 | Herrmann et al. |
| 2009/0275832 A1 | 11/2009 | Gelbart et al. |
| 2009/0275866 A1 | 11/2009 | Gelbart et al. |
| 2009/0299187 A1 | 12/2009 | Bailey et al. |
| 2009/0326468 A1 | 12/2009 | Blier |
| 2010/0036294 A1 | 2/2010 | Mantell et al. |
| 2010/0106086 A1 | 4/2010 | Sudo et al. |
| 2010/0137847 A1 | 6/2010 | Cecchetti et al. |
| 2010/0249671 A1 | 9/2010 | Coleman et al. |
| 2011/0060256 A1 | 3/2011 | Schwarz et al. |
| 2011/0118746 A1 | 5/2011 | Fischer et al. |
| 2012/0035581 A1 | 2/2012 | Travis |
| 2012/0109007 A1 | 5/2012 | Rhad et al. |
| 2012/0271116 A1 | 10/2012 | Koehler |
| 2012/0277750 A1 | 11/2012 | Butsch et al. |
| 2013/0237967 A1 | 9/2013 | Schaeffer et al. |
| 2013/0303979 A1 * | 11/2013 | Stieglitz .............. A61M 3/0283 604/30 |
| 2014/0012194 A1 | 1/2014 | Terwiske et al. |

OTHER PUBLICATIONS

International Searching Authority, Notification of Transmittal of the International Search Report and the Written Opinion for International Application No. PCT/US20121054105, dated Dec. 7, 2012, p. 1-14.

Gore & Associates, Inc, Product Information Sheet, Gore DrySeal Valve, Apr. 10, 2010.

European Patent Office, Extended European Search Report, for International Application No. 14160318.3, dated Aug. 18, 2014, pp. 1-5.

* cited by examiner

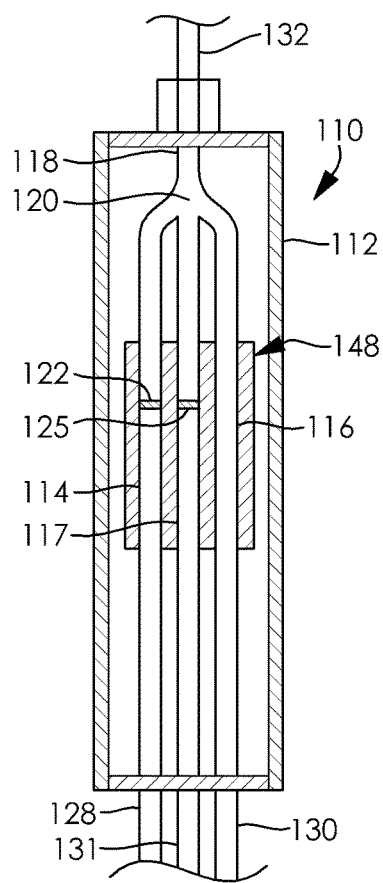
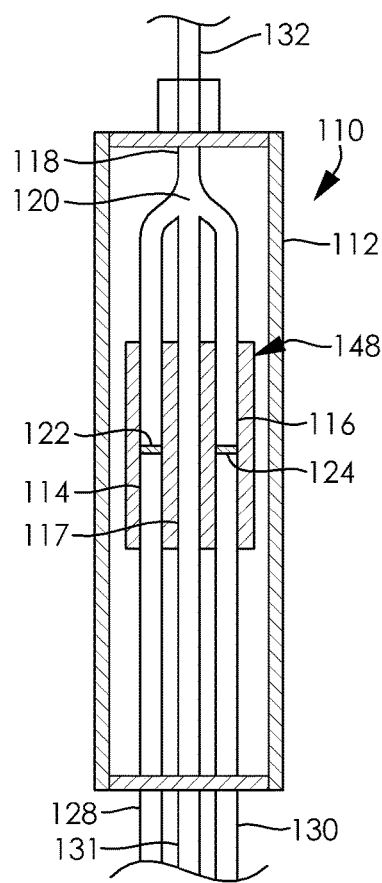
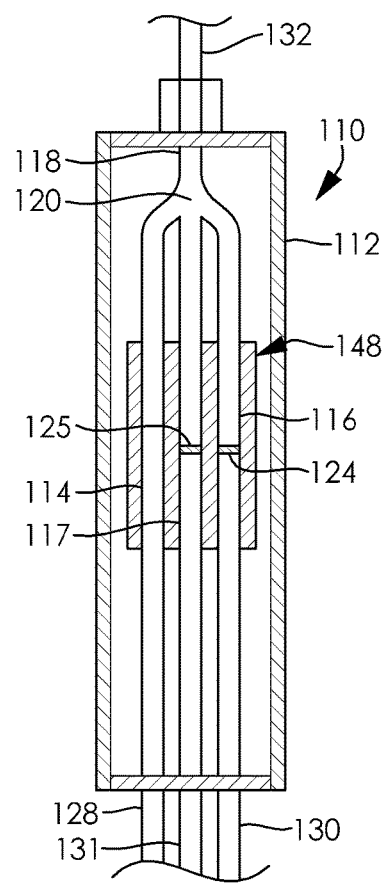
FIG. 6A  FIG. 6B  FIG. 6C

BI-DIRECTIONAL VALVE DEVICE FOR SELECTIVE CONTROL OF FLUID FLOW THROUGH MULTIPLE CONVERGING PATHS

RELATED APPLICATIONS

This application is a continuation of application Ser. No. 15/174,220, filed on Jun. 6, 2016, which is a continuation of application Ser. No. 14/210,821, now U.S. Pat. No. 9,360,124, which was filed on Mar. 14, 2014 and which claims the benefit of provisional application No. 61/786,760, which was filed on Mar. 15, 2013. Each of these related applications is hereby incorporated into this disclosure by this reference.

FIELD

The disclosure relates generally to the field of valve devices for regulating the flow of fluid through fluid paths. The valve devices described in the disclosure are particularly well-suited for use in hand-operated devices, such as medical devices and medical device handles. Specifically described embodiments relate to medical devices for selective suction and irrigation of body passageways.

BACKGROUND

Various clinical procedures require or benefit from the provision of irrigation and suction to a point of treatment. Irrigation allows the clinician to maintain a wet environment for the surrounding tissue while suction provides a tool for removing debris, excess irrigant or other undesirable material from the point of treatment.

Unfortunately, the use of irrigation and suction currently requires the use of separate devices. Thus, in sinus surgery, for example, each time irrigation is desired, the clinician must select a designated irrigation device and advance the device into the nose of the patient before irrigation can be performed. When suction is needed, the irrigation device must be removed from the patient's nose and laid aside. The clinician must then select a designated suction device and advance the device into the nose of the patient before suction can be applied. As a result, many time-consuming device exchanges must be performed, each of which adds time to the procedure and increases the risk for trauma to the patient as additional entries are required.

Thus, a need exists for improved valve devices that allow selective control of multiple fluid paths.

BRIEF SUMMARY OF DESCRIBED EMBODIMENTS

Various example valve devices are described and illustrated herein.

An example valve device comprises a housing defining first and second inlet paths, an outlet path, and a junction in fluid communication with the first and second inlet paths and the outlet path, the housing further defining first and second plunger cavities; a first plunger disposed in the first plunger cavity, the first plunger adapted to move between a first position in which the first plunger impedes fluid flow through the first inlet passage and a second position; a second plunger disposed in the second plunger cavity, the second plunger adapted to move between a first position in which the second plunger impedes fluid flow through the second inlet passage and a second position; and a control member slidably attached to the housing and defining first and second plunger recesses, the first plunger recess sized and configured to receive a portion of the first plunger when the first plunger is in its second position and the second plunger recess sized and configured to receive a portion of the second plunger when the second plunger is in its second position. The control member is movable between a first, proximal position in which the first plunger is in its first position and the second plunger is in its second position and a second, distal position in which the first plunger is in its second position and the second plunger is in its first position.

Another example valve device comprises a housing defining a main body defining an internal chamber and an opening providing access to the internal chamber, and a cradle portion defining first and second inlet paths, an outlet path, a junction in fluid communication with the first and second inlet paths and the outlet path, and first and second plunger cavities; a first plunger disposed in the first plunger cavity, the first plunger adapted to move between a first position in which the first plunger impedes fluid flow through the first inlet passage and a second position; a second plunger disposed in the second plunger cavity, the second plunger adapted to move between a first position in which the second plunger impedes fluid flow through the second inlet passage and a second position; and a control member slidably attached to the housing and defining first and second plunger recesses, the first plunger recess sized and configured to receive a portion of the first plunger when the first plunger is in its second position and the second plunger recess sized and configured to receive a portion of the second plunger when the second plunger is in its second position. The control member is movable between a first, proximal position in which the first plunger is in its first position and the second plunger is in its second position and a second, distal position in which the first plunger is in its second position and the second plunger is in its first position.

Another example valve device comprises a housing defining a main body defining an internal chamber and an opening providing access to the internal chamber, and a cradle portion defining first and second inlet paths, an outlet path, a junction in fluid communication with the first and second inlet paths and the outlet path, first and second plunger cavities, and first and second rails disposed outside of the internal chamber; a first plunger disposed in the first plunger cavity, the first plunger adapted to move between a first position in which the first plunger impedes fluid flow through the first inlet passage and a second position; a second plunger disposed in the second plunger cavity, the second plunger adapted to move between a first position in which the second plunger impedes fluid flow through the second inlet passage and a second position; and a control member slidably attached to the housing and defining a first channel that receives the first rail, a second channel that receives the second rail, and first and second plunger recesses, the first plunger recess sized and configured to receive a portion of the first plunger when the first plunger is in its second position and the second plunger recess sized and configured to receive a portion of the second plunger when the second plunger is in its second position. The control member is movable between a first, proximal position in which the first plunger is in its first position and the second plunger is in its second position and a second, distal position in which the first plunger is in its second position and the second plunger is in its first position Additional understanding of the inventive valve devices can be obtained with review of the detailed description, below, and the appended drawings.

BRIEF DESCRIPTION OF THE DRAWINGS

FIG. 6A is a sectional view of a second example valve device. In this figure, the control member is in a first, proximal position.

FIG. 6B is a sectional view of the second example valve device. In this figure, the control member is in a second, intermediate position.

FIG. 6C is a sectional view of the second example valve device. In this figure, the control member is in a third, distal position.

DETAILED DESCRIPTION OF ILLUSTRATED EMBODIMENTS

Figure 1:
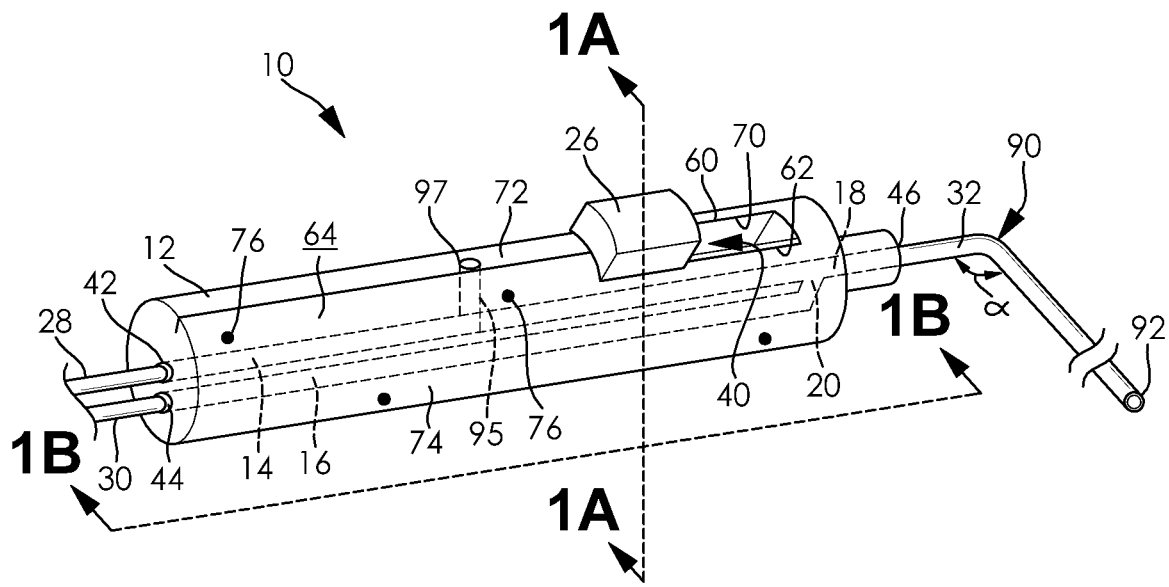
FIG. 1 is a perspective view of a first example valve device having a control member in a first, proximal position.

The following detailed description and the appended drawings describe and illustrate various example valve devices. The description and drawings are exemplary in nature and are provided to enable one skilled in the art to make and use one or more example valve devices. They are not intended to limit the scope of the claims in any manner.

FIGS. 1, 1A, 1B, 2, 2A and 2B illustrate a first example valve device 10. Valve device 10 includes a housing 12, first 14 and second 16 inlet paths, outlet path 18, and junction 20 joining the first 14 and second 16 inlet paths and the outlet path 18. A first plunger 22 is partially disposed in the first inlet path 14 and is movable between first and second positions. Similarly, a second plunger 24 is partially disposed in the second inlet path 16 and is movable between first and second positions. A control member 26 is slidably disposed on the housing 12 and is movable between a first, proximal position, illustrated in FIGS. 1, 1A and 1B, and a second, distal position, illustrated in FIGS. 2, 2A and 2B. In the illustrated embodiment, first 28 and second 30 tubular members are partially disposed in the first 14 and second 16 inlet paths, respectively. Also, an outlet tubular member 32 is partially disposed in the outlet path 18.

Figure 1A:
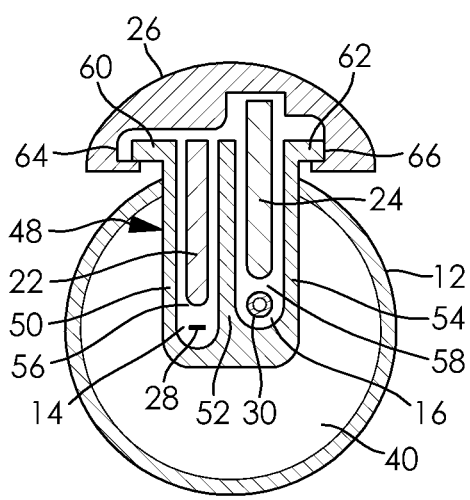
FIG. 1A is a sectional view of the valve device illustrated in FIG. 1, taken along line 1A-1A.
Figure 1B:
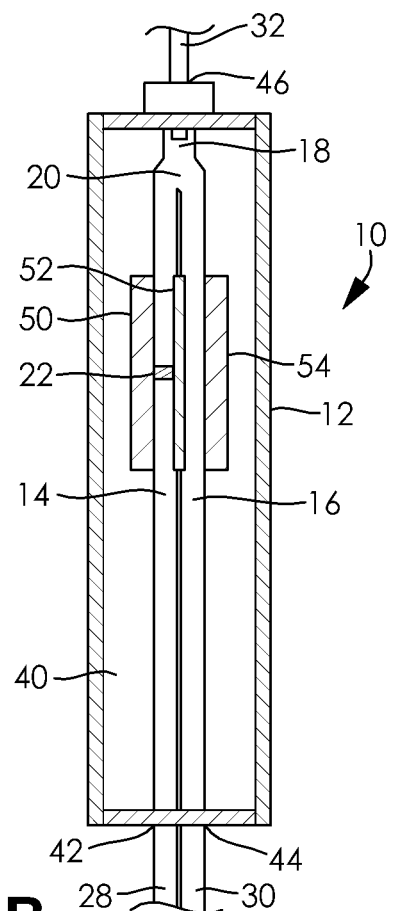
FIG. 1B is a sectional view of the valve device illustrated in FIG. 1, taken along line 1B-1B.
Figure 2:
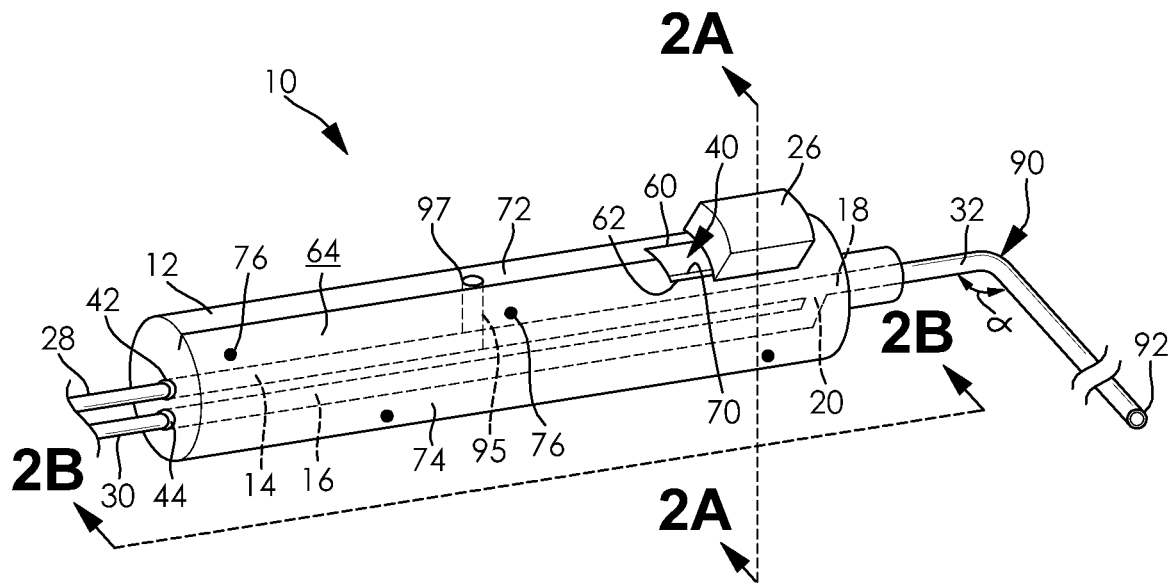
FIG. 2 is another perspective view of a first example valve device. In this figure, the control member is in a second, distal position.
Figure 2A:
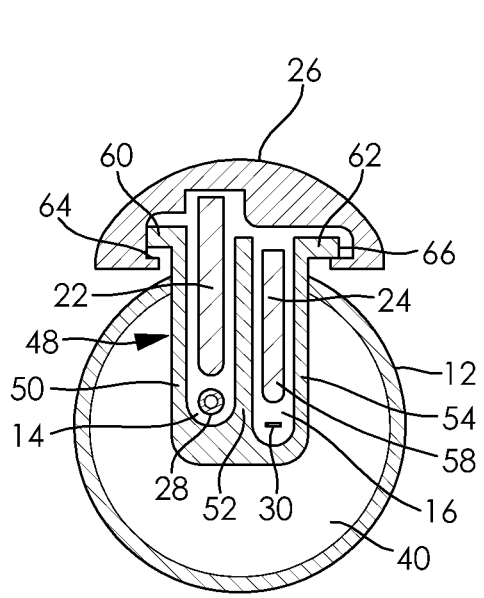
FIG. 2A is a sectional view of the valve device illustrated in FIG. 2, taken along line 2A-2A.
Figure 2B:
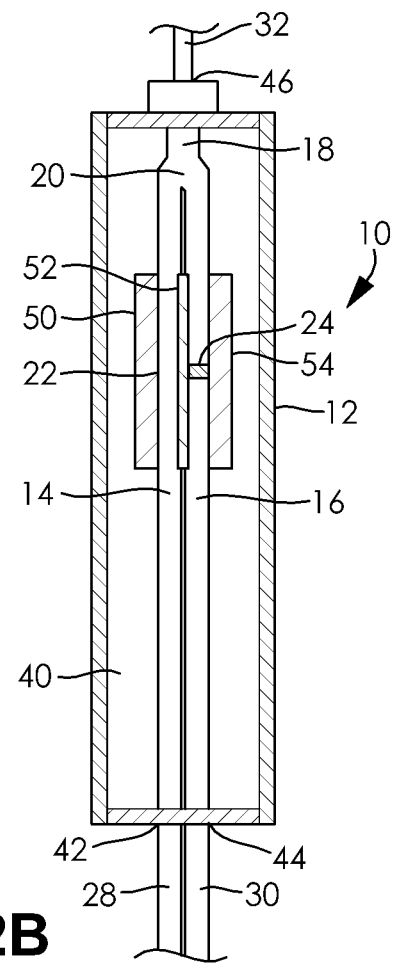
FIG. 2B is a sectional view of the valve device illustrated in FIG. 2, taken along line 2B-2B.

Each of the plungers 22, 24 provides a barrier to fluid flow through the respective inlet path 14, 16 when in its first position, but provides no barrier or less of a barrier to fluid flow through the respective inlet path 14, 16 when in its second position. As best illustrated in FIG. 1A, the control member 26 maintains the first plunger 22 in its first position and provides a barrier that prevents the first plunger 22 from moving to its second position when the control member 26 is in the first, proximal position. Also while in the first, proximal position, the control member 26 receives a portion of the second plunger 24, allowing it to be positioned in its second position. In contrast, and as best illustrated in FIG. 2A, the control member 26 maintains the second plunger 24 in its first position and provides a barrier that prevents the second plunger 24 from moving to its second position when the control member 26 is in the second, distal position. Also while in the second, distal position, the control member 26 receives a portion of the first plunger 22, allowing it to be positioned in its second position. Each plunger in a valve device according to a particular embodiment can have any suitable structure and configuration; the illustrated structures are examples of suitable structures. Another example of a suitable structure is a plunger that defines an aperture through its thickness. With these plungers, the aperture defines a passageway through the plunger that is in communication with the inlet path with which the plunger is associated when the plunger is in its second position, thereby allowing fluid flow through the inlet path and the aperture. When in the plunger is in its first position, however, the aperture is out of alignment with the inlet path and provides a barrier to fluid flow through the inlet path.

Movement of the control member 26 between its first, proximal and second, distal positions results in movement of each of the plungers 22, 24 between its first and second positions, but in opposite orders. Thus, movement of the control member 26 between its first, proximal and second, distal positions controls fluid flow through the inlet paths 14, 16 and into the junction 20 and outlet path 18. For example, movement of the control member 26 from the first, proximal position, best illustrated in FIG. 1, to the second, distal position, best illustrated in FIG. 2, forces the first plunger 22 to move from its first position, in which it blocks fluid flow through inlet path 14 as best illustrated in FIG. 1A, to its second position, in which it provides no barrier or less of a barrier to fluid flow through inlet path 14 as best illustrated in FIG. 2A. In contrast, movement of the control member 26 from the second, distal position, best illustrated in FIG. 2, to the first, proximal position, best illustrated in FIG. 1, forces the second plunger 24 to move from its first position, in which it blocks fluid flow through inlet path 16 as best illustrated in FIG. 2A, to its second position, in which it provides no barrier or less of a barrier to fluid flow through inlet path 16 as best illustrated in FIG. 1A. As such, movement of the control member 26 between its first, proximal and second, distal positions provides selective control over fluid flow through the inlet paths 14, 16 and into the junction 20 and outlet path.

In the illustrated embodiment, housing 12 defines an internal chamber 40 within which the first 28 and second 30 inlet tubular members and the outlet tubular member 32 are partially inserted. In this embodiment, each of the first 28 and second 30 inlet tubular members recoils in response to being compressed by the respective plunger 22, 24 following the appropriate movement of the control member 26, as described above. As such, housing 12 defines first 42 and second 44 openings that provide fluid communication to the first 14 and second 16 inlet paths, respectively. Also, housing 12 defines a third opening 46 that provides fluid communication to the outlet path 18. It is noted that internal chamber can have any suitable size, shape and configuration, and the illustrated chamber is exemplary in nature. Also, the internal chamber is considered optional. For example, a solid form housing can be used, essentially eliminating the internal chamber.

Also in the illustrated embodiment, housing 12 defines cradle portion 48 that defines the first 14 and second 16 inlet paths, the junction 20 and the outlet path 18. Cradle portion 48 also defines first 50, second 52 and third 54 wall portions that cooperatively define first 56 and second 58 plunger cavities. As best illustrated in FIGS. 1A and 2A, first 50 and second 52 wall portions cooperatively define first plunger cavity 56, within which the first plunger 22 is disposed and able to move between its first and second positions. Similarly, second 52 and third 54 wall portions cooperatively define second plunger cavity 58, within which the second plunger 24 is disposed and able to move between its first and second positions.

Also in the illustrated embodiment, housing 12 defines first 60 and second 62 rails that are disposed outside of the internal chamber 40 and above a main external surface 64 of the housing 12. As best illustrated in FIGS. 1A and 2A, control member 26 defines complimentary channels 64, 66 that receive the first 60 and second 62 rails. The interface between rails 60, 62 and channels 64, 66 allows the control member 26 to move slidably along the housing and affect the movement of the plungers 22, 24, and the overall operation of the valve device 10, as described above.

Also in the illustrated embodiment, housing 12 defines opening 70 between the internal chamber 40 and the environment external to the housing 12. Cradle portion 48 is disposed through opening 70 such that a first portion of the cradle portion 48 is disposed within the internal chamber 40 and a second portion of the cradle portion 48 is disposed outside of the internal chamber 40.

In the illustrated embodiment, housing 12 defines ancillary passageway 95 that is positioned proximal to the control member 26 and that is in fluid communication with the first inlet path 14. Ancillary passageway 95 terminates in opening 97 on the external surface 64 of the housing 12. While inclusion of the ancillary passageway 95 is considered optional, it is also considered advantageous for inclusion in valve devices intended to be used with suction because it provides a degree of manual control over the suction. For example, if inlet tubular member 28, and therefore inlet path 14, of valve device 14 were connected to a suction source, a clinician can use a finger, thumb or other item to cover opening 97, effectively forcing the suction source to draw fluid through the inlet path 14 instead of through the ancillary passageway 95. This provides an additional degree of control over the flow of fluid through the inlet path and the inlet tubular member, if included, of these particular valve devices.

Housing 12 can have any suitable size, shape and configuration, and a skilled artisan will be able to select an appropriate size, shape and configuration for a valve device according to a particular embodiment based on various considerations, including the intended use of the valve device. For example, in the illustrated embodiment, housing 12 has a cylindrical configuration with the opening 40 and control member 26 positioned toward the distal end of the valve device (toward the outlet path 18 in the figures). The inventors have determined that this configuration is suitable for valve devices intended to be used in hand-operated medical devices, such as suction/irrigation devices.

It is also noted that the housing can comprise a unitary member or can comprise two or more separate members that are attached to form the housing. For example, in the illustrated embodiment, housing 12 is formed of housing members 72, 74 that are attached to each other with a series of connectors 76. In these embodiments, any suitable connectors can be used, including rivets, screws, adhesives, and the like. The housing submembers 72, 74 can also be structured to allow a mechanical interaction between them that is sufficient to provide the desired attachment. Also in the illustrated embodiment, cradle portion 48 is a separate member that is attached to the housing submembers 72, 74 to form housing 12. Any suitable connectors can be used in attaching the cradle portion 48 to the housing submembers 72, 74, including rivets, screws, adhesives, welds, and the like. Furthermore, any suitable technique or process can be used in attaching the cradle portion 48 to the housing submembers 72, 74, including ultrasonic welding, gluing, riveting, screwing, and the like. The components can also be structured to allow a mechanical interaction between the cradle portion 48 and the housing submembers 72, 74 that is sufficient to provide the desired attachment. Alternatively, the cradle portion 48 can be defined by one or both of the housing submembers 72, 74, or a unitary housing can define the cradle portion 48.

Furthermore, housing 12 can be formed of any suitable material, and a skilled artisan will be able to select an appropriate material for a valve device according to a particular embodiment based on various considerations, including the intended lifespan of the valve device (e.g., single use v. reusable) and any treatment processes to which the valve device is expected to be exposed (e.g., sterilization processes). Examples of suitable materials include plastics and metals commonly used in the fabrication of medical devices and/or medical equipment.

Figure 3:
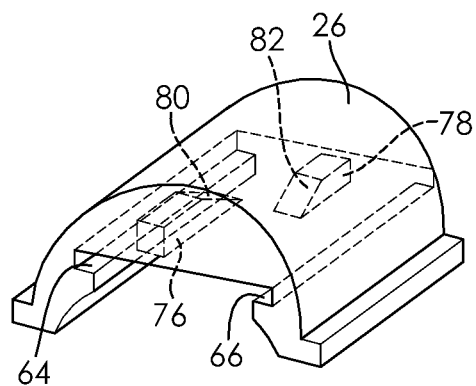
FIG. 3 is a perspective view of a control member isolated from a first example valve device.
Figure 4:
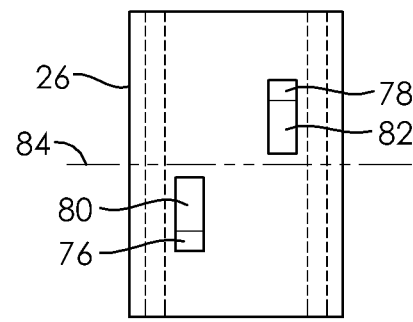
FIG. 4 is a top view of the control member illustrated in FIG. 3.
Figure 7:
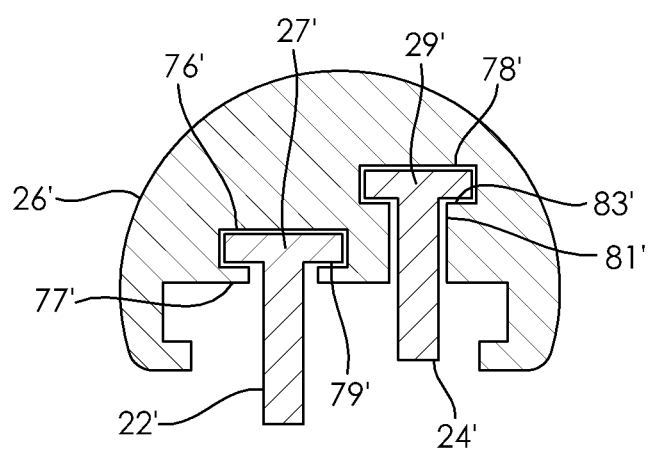
FIG. 7 is a sectional view of another example control member.

As best illustrated in FIGS. 3 and 4, control member 26 defines first 76 and second 78 recesses that are sized and configured to receive a portion of the first 22 and second 24 plungers, respectively. In the illustrated embodiment, control member 26 includes a first ramped surface 80 that defines one wall of the first recess 76 and a second ramped surface 82 that defines one wall of the second recess 78. The recesses 76, 78 are oriented opposite one another with respect to a hypothetical line 84 such that the ramped surfaces 80, 82 extend upward and away from each other. This arrangement of the recesses 76, 78 ensures that only one of the plungers 22, 24 is fully seated in its respective recess 76, 78 at any given time as the control member 26 is moved between its first, proximal and second, distal positions. In alternative embodiments, an example of which is illustrated in FIG. 7, each of the recesses 76', 78' defines a shoulder that forms a track, such as shoulders 77' and 81' and tracks 79' and 83'. In these embodiments, each of the tracks 79', 81' receives a flange defined by or disposed on the upper portion of the respective plunger 22', 24'. Thus, flange 27' is received by track 79' and flange 29' is received by track 81'. Each of the flanges 27', 29' rides within the respective track 79', 81' such that the control member 26' pushes the respective plunger 22', 24' upward and pulls the plunger 22', 24' downward with appropriate movement of the control member 26', as described above. In these alternative embodiments, the tracks can be formed as recesses within the control member, as a recess defined between multiple pieces that are assembled to form the control member, or in any other suitable manner. These alternative embodiments avoid reliance on recoil of a tubular member compressed by a plunger to move the plunger back to its upper position.

Figure 4A:
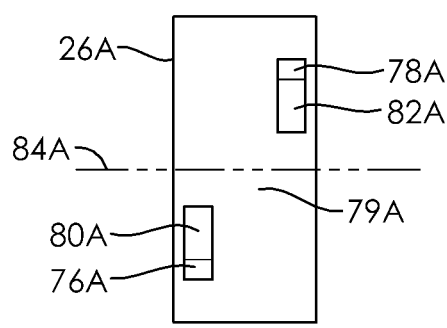
FIG. 4A is a top view of an alternative control member.

The control member 26 illustrated in FIG. 4 is suitable for use in valve devices in which it is desired to have fluid flowing through one of the inlet paths at any given time. As illustrated in FIG. 4, each of the recesses 76, 78 extends from hypothetical line 84. Thus, any proximally- or distally-directed movement of the control member 26 relative to the hypothetical line 84 results in one of the plungers 22, 24 initiating movement into the respective plunger cavity 56, 58. While this is desirable in some embodiments, an intermediate position in which fluid cannot flow through either inlet path may be desirable in others. For these embodiments, each of the recesses can be spaced from the hypothetical line by a suitable distance. For example, as illustrated in FIG. 4A, an alternative control member 26A can include recesses 76A, 78A, each of which extends from a point that is spaced from the hypothetical midline 84A, providing an intermediate space 79A between the two recesses 76A, 78A that does not define a recess. As a result, when this control member 26A is positioned in an intermediate position, between its first, proximal position and its second, distal position, both plungers are maintained in their first position within the respective plunger cavities of the valve device, blocking fluid flow through each of the respective inlet paths. This structural arrangement can be scaled for control members that include more than two recesses, also by including an appropriate spacing between pairs of recesses. In these embodiments, individual pairs of recessed can all include a space of the same size, or different sizes. Some pairs can have no spacing, also, such as the recesses 76, 78 of the control member 26 illustrated in FIG. 4. This structural arrangement is considered advantageous at least because it provides an additional degree of control over fluid flow through the inlet paths.

Figure 5:
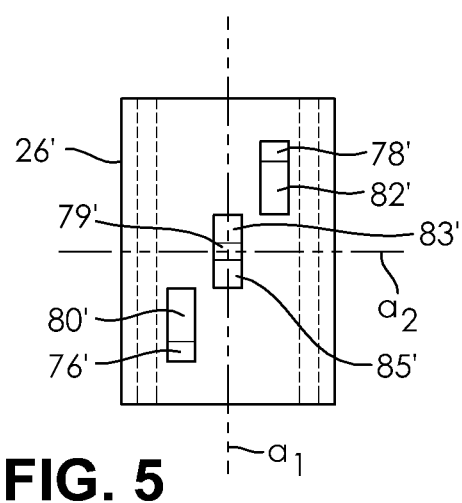
FIG. 5 is a top view of another alternative control member.

It is noted that a valve device according to an embodiment can include more than two inlet paths that converge into a single outlet path. In these embodiments, the cradle portion defines the additional inlet path(s), and the control member defines additional recess(es). FIG. 5 illustrates an alternative control member 26' suitable for use in a valve device having three inlet paths. This control member 26' defines first 76', second 78' and third 79' recesses. The third recess 79' is diposed between the first 76' and second 78' recesses with respect to both a lengthwise axis $a_1$ and a transverse axis $a_2$ of the control member 26'. The first 76' and second 78' recesses have structures similar to those in the control member 26 illustrated in FIGS. 3 and 4. Thus, control member 26' includes a first ramped surface 80' that defines one wall of the first recess 76' and a second ramped surface 82' that defines one wall of the second recess 78'. The recesses 76', 78' are oriented opposite one another with respect to transverse axis $a_2$ such that the ramped surfaces 80, 82 extend upward and away from each other. In this embodiment, control member 26' also defines third 83' and fourth 85' ramped surfaces, each of which defines one wall of the third recess 79'. The third 83' and fourth 85' ramped surfaces are positioned such that each extends upward and toward the center of the third recess 79'. This arrangement of the recesses 76', 78', 79' allows the control member 26' to control fluid flow through three inlet paths and ensures that only one of three plungers in an associated valve device is fully seated in its respective recess 76', 78', 79' at any given time as the control member 26' is moved between first, proximal, intermediate, and second, distal positions.

While inclusion of inlet tubular members 28, 30 and outlet tubular member 32 is considered optional, inclusion of these components can be advantageous at least because it allows the valve device 10 to control fluid flow from and into remote locations. For example, one of the inlet tubular member 28 can be placed in fluid communication with a supply of an irrigation fluid and the other inlet tubular member 30 can be connected to a vacuum or others source of negative air pressure. When the outlet tubular member 32 is positioned at a desired point of treatment, the control member 26 can be moved between its first, proximal position and second, distal position to selectively deliver irrigation fluid to the point of treatment and apply suction to the point of treatment.

If included, inlet tubular members 28, 30 and outlet tubular member 32 can be formed from any suitable material and can have any suitable configuration. A skilled artisan will be able to select an appropriate material and configuration for each based in a valve device according to particular embodiment based on various considerations. The inventors have determined that inlet tubular members 28, 30 formed of a flexible and resilient material, such as a polymeric material, are advantageous at least because the plungers can pinch tubular members formed of such materials when blocking fluid flow through the tubular member is desired, and the tubular member easily restores itself to an open configuration when the plunger moves from its first position to its second position, effectively removing the pinching effect. Indeed, these tubular members can ensure that the plunger remains in its second position, which allows fluid flow through the tubular member, until the control member moves the plunger to its first position and pinches the tubular member. Examples of suitable materials for the inlet tubular members include silicone tubing known in the art. The inventors have also determined that a metal tubular member, such as a stainless steel tubular member, is suitable for the outlet tubular member at least because the rigidity of such a tubular member provides desirable handling characteristics when delivering fluid to and taking fluid away from a point of treatment. Other examples of suitable materials for the outlet tubular member include polymer-like rigid nylon, polyether ether ketone (PEEK), cobalt chromium, nickel titanium alloys, and others.

Also, if included, inlet tubular members 28, 30 and outlet tubular member 32 can have any suitable size, shape and configuration, and a skilled artisan will be able to select an appropriate size, shape and configuration for each included tubular member in a valve device according to a particular embodiment based on various considerations, including the fluids with which the valve device is intended to be used and the point or points of treatment at which the valve device is intended to be used. If included, inlet tubular members are advantageously elongate tubular members having a circular or ovoid cross-sectional shape and inner passageway cross-sectional shape. If included, the outlet tubular member advantageously defines a structural feature, such as a bend, curve, curves, helix or other structural feature that facilitates placement of the distal end, and distal opening, of the outlet tubular member in or near the point of treatment at which the particular valve device is intended to be used. For example, in the first example embodiment and as best illustrated in FIGS. 1 and 2, it is considered advantageous to include a bend 90 in the outlet tubular member 32 to facilitate placement of the distal end 92 of the outlet tubular member 32 in or near a sinus passageway of a patient during sinus surgery and/or to allow for spatial separation of a clinician's hands when using both the valve device 10 and another device, such as a scope, in a procedure. If included, bend 90 can have any suitable angle, and a skilled artisan will be able to select an appropriate angle for a valve device according to a particular embodiment based on various considerations, including the tortuosity of the body cavity, passageway or other feature leading to or containing the point of treatment at which the valve device is intended to be used. As illustrated in FIGS. 1 and 2, bend 90 can have an angle α that maintains the axis of the passageway defined by the outlet tubular member 32 on a single plane and that is between about 90° and about 180°. Other examples of suitable angles include angles between about 115° and about 150°, and an angle of about 135°.

FIGS. 6A, 6B and 6C illustrate a second example valve device 110. The second example valve device 110 is similar to the first example valve device 10 illustrated in FIGS. 1, 1A, 1B, 2, 2A and 2B, except as described below. Thus, valve device 110 includes a housing 112, first 114 and second 116 inlet paths, outlet path 118, and junction 120 joining the first 114 and second 116 inlet paths and the outlet path 118. A first plunger 122 is partially disposed in the first inlet path 114 and is movable between first and second positions. Similarly, a second plunger 124 is partially disposed in the second inlet path 116 and is movable between first and second positions. A control member (not illustrated in the FIGS. 6A, 6B and 6C) is slidably disposed on the housing 12. For this embodiment, control member 26' illustrated in FIG. 5 is suitable for inclusion in the valve device 110.

In this embodiment, the cradle portion 148 of the housing 112 defines a third inlet path 117 that is in fluid communication with the junction 120. Also, the valve device 110 includes a third plunger 125 that is partially disposed in the third inlet path 117 and is movable between first and second positions similar to the first 122 and second plungers 124. Thus, in this embodiment, movement of the control mechanism from a first, proximal position to a second, intermediate position, to a third, distal position produces selective, individual movement of the first 122, second 124, and third 125 plungers. In turn, this allows a user to selectively control through which of the first 128, second 130 and third 131 inlet tubular members fluid flow is allowed to pass at any given time to the junction 120 and, ultimately the outlet tubular member, or in the opposite direction.

In FIG. 6A, control member (not illustrated) is in a first, proximal position. In this position, the control member maintains the first 122 and third 125 plungers in their first positions by blocking these plungers 122, 125 from moving to their second position. The second plunger (not visible in FIG. 6A), however, is able to move to its second position. As a result, fluid flow through the first 114 and third 117 inlet paths is blocked while the second inlet path 116 is open to fluid flow.

In FIG. 6B, control member (not illustrated) is in a second, intermediate position. In this position, the control member maintains the first 122 and second 124 plungers in their first positions by blocking these plungers 122, 124 from moving to their second position. The third plunger (not visible in FIG. 6B), however, is able to move to its second position. As a result, fluid flow through the first 114 and second 116 inlet paths is blocked while the third inlet path 117 is open to fluid flow.

In FIG. 6C, control member (not illustrated) is in a third, distal position. In this position, the control member maintains the second 124 and third 125 plungers in their first positions by blocking these plungers 124, 125 from moving to their second position. The first plunger (not visible in FIG. 6C), however, is able to move to its second position. As a result, fluid flow through the second 116 and third 117 inlet paths is blocked while the first inlet path 114 is open to fluid flow.

The foregoing detailed description refers to example valve devices and includes the best mode for practicing the invention. The description and the appended drawings illustrating the described devices are intended only to provide examples and not to limit the scope of the claims in any manner.

What is claimed is:

1. A hand-operated suction and irrigation medical device, comprising:
   a housing having a proximal end and a distal end and defining a first inlet path, a second inlet path, and an outlet path;
   a first tubular member partially disposed within the first inlet path and extending from the proximal end of the housing in a first direction;
   a second tubular member partially disposed within the second inlet path and extending from the proximal end of the housing in the first direction;
   a third tubular member partially disposed within the outlet path and extending from the distal end of the housing in a second direction;
   a control member slidably disposed on the housing, the control member movable between a first, proximal position and a second, distal position; and
   a passageway providing fluid communication between the first inlet path and an environment external to the housing such that covering the passageway provides control over a flow of fluid through the first inlet path and the first tubular member.

2. The medical device of claim 1, wherein the first direction is substantially opposite the second direction.

3. The medical device of claim 1, wherein the third tubular member comprises a metal.

4. The medical device of claim 3, wherein the metal comprises stainless steel.

5. The medical device of claim 1, wherein the third tubular member comprises a bend spaced from the distal end of the housing.

6. The medical device of claim 5, wherein the bend defines an angle that is between about 90 degrees and about 180 degrees.

7. The medical device of claim 5, Wherein the bend defines an angle that is between about 115 degrees and about 150 degrees.

8. The medical device of claim 5, wherein the bend defines an angle that is about 135 degrees.

9. The medical device of claim 1, wherein the housing has an external surface; and
   wherein the passageway terminates in opening disposed on the external surface of the housing.

10. The medical device of claim 9, wherein the opening is positioned between the proximal and distal ends of the housing.

11. The medical device of claim 9, wherein the opening is positioned between the proximal end of the housing and the control member.

12. A hand-operated suction and irrigation medical device, comprising:
    a housing having a proximal end and a distal end and defining a first inlet path, a second inlet path, and an outlet path;
    a first tubular member partially disposed within the first inlet path and extending from the proximal end of the housing in a first direction;
    a second tubular member partially disposed within the second inlet path and extending from the proximal end of the housing in the first direction;
    a third tubular member partially disposed within the outlet path and extending from the distal end of the housing in a second, different direction;
    a control member slidably disposed on the housing, the control member movable between a first, proximal position and a second, distal position; and a passageway disposed between the proximal and distal ends of the housing and extending from the first inlet path to an opening to an environment external to the housing;

wherein covering the opening provides control over a flow of fluid throw the first inlet path and the first tubular member.

13. The medical device of claim 12, wherein the third tubular member comprises a metal.

14. The medical device of claim 13, wherein the metal comprises stainless steel.

15. The medical device of claim 12, wherein the third tubular member comprises a bend spaced from the distal end of the housing.

16. The medical device of claim 15, wherein the bend defines an angle that is between about 90 degrees and about 180 degrees.

17. The medical device of claim 15, wherein the bend defines an angle that is between about 115 degrees and about 150 degrees.

18. The medical device of claim 15, wherein the bend defines an angle that is about 135 degrees.

19. A hand-operated suction and irrigation medical device, comprising:

a housing having a proximal end and a distal end and defining a first inlet path, a second inlet path, and an outlet path;

a first tubular member partially disposed within the first inlet path and extending from the proximal end of the housing in a first direction;

a second tubular member partially disposed within the second inlet path and extending from the proximal end of the housing in the first direction;

a third tubular member partially disposed within the outlet path and extending from the distal end of the housing in a second, different direction, the third tubular member comprising a bend spaced from the distal end of the housing;

a control member slidably disposed on the housing, the control member movable between a first, proximal position and a second, distal position; and a passageway disposed between the proximal and distal ends of the housing and extending from the first inlet path to an opening to an environment external to the housing, the passageway providing fluid communication, between the first inlet path and the environment external to the housing.

20. The medical device of claim 19, wherein the angle is between about 115 degrees and about 150 degrees.

* * * * *

UNITED STATES PATENT AND TRADEMARK OFFICE
CERTIFICATE OF CORRECTION

| | | |
|---|---|---|
| PATENT NO. | : 11,035,481 B2 | Page 1 of 1 |
| APPLICATION NO. | : 15/990683 | |
| DATED | : June 15, 2021 | |
| INVENTOR(S) | : Darin Schaeffer and Jeffry Melsheimer | |

It is certified that error appears in the above-identified patent and that said Letters Patent is hereby corrected as shown below:

In the Claims

Column 10, Claim 7, Line 36, Please correct:
"Wherein"
To:
--wherein--;

Column 10, Claim 9, Line 43, Please correct:
"terminates in opening disposed"
To:
--terminates in an opening disposed--.

Signed and Sealed this
Twenty-sixth Day of October, 2021

Drew Hirshfeld
*Performing the Functions and Duties of the*
*Under Secretary of Commerce for Intellectual Property and*
*Director of the United States Patent and Trademark Office*